United States Patent
Bratz et al.

(10) Patent No.: US 6,869,914 B2
(45) Date of Patent: Mar. 22, 2005

(54) PROCESS FOR THE PREPARATION OF SOLVENT-FREE SUSPENSIONS

(75) Inventors: Matthias Bratz, Limburgerhof (DE); Karl-Friedrich Jäger, Limburgerhof (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 43 days.

(21) Appl. No.: 10/319,714

(22) Filed: Dec. 16, 2002

(65) Prior Publication Data

US 2003/0148887 A1 Aug. 7, 2003

(30) Foreign Application Priority Data

Dec. 17, 2001 (DE) .......................................... 101 62 059

(51) Int. Cl.$^7$ ............................................... A01N 25/08

(52) U.S. Cl. ...................... 504/339; 504/347; 504/362; 504/367; 514/356; 514/404; 514/407; 514/539; 514/952

(58) Field of Search ................................. 504/339, 347, 504/362, 367; 514/356, 404, 407, 539, 952

(56) References Cited

U.S. PATENT DOCUMENTS

| 4,571,088 A | * | 2/1986 | Frensch et al. .............. 366/136 |
| 5,137,726 A | | 8/1992 | Ogawa et al. ............... 424/405 |
| 6,541,426 B1 | * | 4/2003 | Kostansek et al. .......... 504/341 |

FOREIGN PATENT DOCUMENTS

| EP | 0 112 438 | 7/1984 |
| EP | 1 060 667 | 12/2000 |
| WO | WO 93/14632 | 8/1993 |

* cited by examiner

Primary Examiner—S. Mark Clardy
(74) Attorney, Agent, or Firm—Keil & Weinkauf

(57) ABSTRACT

A process for the preparation of a solvent-free suspension of a low-melting point water-insoluble solid agrochemical active ingredient, which comprises suspending 1–40% by weight of a silica-based carrier in 40 to 97% by weight of water in the presence of 1–40% by weight of anionic dispersant, heating the suspension thus obtained to a temperature above that of the active ingredient, and adding, with stirring, 1–25% by weight of a molten active ingredient with a melting point of <80° C. or a mixture of at least two active ingredients each having a melting point of <80° C. The present invention furthermore relates to the preparation of suspension concentrates, water-dispersible powders and water-dispersible granules based on the suspensions prepared via the abovementioned process.

12 Claims, No Drawings

PROCESS FOR THE PREPARATION OF SOLVENT-FREE SUSPENSIONS

The present invention relates to a process for the preparation of a solvent-free suspension of low-melting-point water-insoluble solid agrochemical active ingredients, which comprises
  a) suspending 1–40% by weight of a silica-based carrier in 40 to 97% by weight of water in the presence of 1–40% by weight of anionic dispersant,
  b) heating the suspension obtained in step a) to a temperature above that of the active ingredient, and
  c) adding, with stirring, 1–25% by weight of the molten water-insoluble active ingredient with a melting point of <80° C. or a mixture of molten water-insoluble active ingredients, where each component of the mixture has a melting point of <80° C.,
where the quantities stated in a) and c) total 100% by weight.

The invention furthermore relates to the preparation of suspension concentrates, water-dispersible powders and water-dispersible granules based on the suspensions prepared via the abovementioned process.

Particulate, solvent-free formulations are widely used in crop protection, owing to their advantageous properties. In particulate formulations, the active ingredient exists as a defined particle and will also be in particulate or dissolved form after preparing the spray mixture in diluted form. We can distinguish between solid forms such as water-dispersible granules (WG formulations) and water-dispersible powders (WP formulations) and flowable forms such as suspension concentrates (SC formulations).

The finely particulate form which has been mentioned above is essential not only for the storage stability of the concentrated commercially available products (for example SCs), but also for the stability of the spray mixtures prepared from the corresponding commercially available products.

In the preparation of solid formulations (WP, WG), the finely particulate form can be achieved by milling active ingredient, in general together with adjuvants. A variety of processes are available for this purpose. We can distinguish between dry-milling, for example via hammer mills or air-jet mills, and milling in liquid phase, such as, for example, in agitated ball mills. In most cases, water is used as the liquid phase. To achieve the desired fineness, it may be necessary to repeat the milling passage several times.

However, the above-described process is particularly suitable for high-melting active ingredients. The abovementioned procedures are problematic for low-melting-point water-insoluble active ingredients, i.e. active ingredients with a melting point of below 80° C. and solubility in water of less than 1000 mg/l at 20° C., since, in the case of these active ingredients, the energy input during the milling process frequently leads to partial or complete melting of the active ingredient, which, in a number of cases, leads to unsatisfactory product quality or to clogging of the mill owing to the aggregation of active ingredients.

Other processes described in the literature for the preparation of solid formulations such as WPs or WGs comprising low-melting-point active ingredients are disadvantageous owing to the passes to be carried out, since high-volume solids with disadvantageous toxicological properties must be handled in mixers and mills. This applies in particular to the handling of finely particulate particles loaded with active ingredient.

Thus, WO 93/14632 describes the formulation of low-melting-point active ingredients by intimately grinding the active ingredient in question together with a suitable carrier, with the simultaneous high energy input (high energy milling). To achieve a sufficient distribution of the molten active ingredient on the carrier, the carriers used for this purpose, which are based on minerals or clay, are preferably pulverulent and have a small particle size. The resulting solid mixture is subsequently milled and further processed.

The processes for the preparation of water-dispersible granules which are described in EP-A 112438 are again based on mixing the solid ingredients, followed by repeated dry milling.

A process described in DE 4013028 A1 is based on warming the active ingredient in an organic solvent and adding the mixture to an aqueous preparation comprising dextrin or lactose as solid carrier. The resulting emulsion is subsequently spray-dried. A disadvantage of this process is the use of the additional organic solvent and the high price of the dextrins to be used.

Liquid concentrates comprising a low-melting-point water-insoluble active ingredient are generally prepared by milling the abovementioned active ingredient in the presence of various adjuvants and of water as the continuous medium (Mollet, H. and Grubemann, A. "Formulierungstechnik" [Formulation Technology], WILEY-VCH, 2000, p. 133 et seq.). This process, which is widely used in practice, has the disadvantage that some or all of the active ingredient melts during the milling and in the course of storage, which, in turn, has an adverse effect on product quality.

Other processes used in practice also have considerable disadvantages:

In EP-A 1060667, a stream of molten active ingredient and surfactant is mixed with a second stream (essentially water) and subsequently mixed in a chamber using high shearing forces, during which process the active ingredient melts. Subsequent cooling gives rise to finely dispersed active ingredient. This procedure is complicated since several steps and a high energy input are required. A solid carrier to which the active ingredient is applied, for example, is not used in this process.

It is an object of the present invention to find suitable processes for the preparation of particulate stable formulations specifically for low-melting-point active ingredients while avoiding the use of organic solvents.

This object is achieved by providing a process for the preparation of a suspension of low-melting-point water-insoluble solid agrochemical active ingredients, which comprises
  a) suspending 1–40% by weight of a silica-based carrier in 40 to 97% by weight of water in the presence of 1–40% by weight of an anionic dispersant,
  b) heating the suspension obtained in step a) and
  c) adding, with stirring, 1–25% by weight of the molten water-insoluble active ingredient with a melting point of <80° C. or a mixture of molten water-insoluble active ingredients, where each component of the mixture has a melting point of <80° C.,
where the quantities stated in a) and c) total 100% by weight. The suspension according to the invention furthermore comprises at least 40% by weight of water.

In the present context, a water-insoluble active ingredient is understood as meaning an active ingredient which has a solubility in water of less than 1000 mg/l at 20° C.

In the context of step b), the suspension is heated at a temperature which is at least 5° C., preferably 10° C., especially preferably 20° C., above the temperature of the active ingredient.

The quantity of active ingredient which is added in step c) amounts to 1–25% by weight, preferably 2–20% by weight, especially preferably 4–10% by weight, based on the total mixture.

Stirring in step c) can be achieved by means of customary stirrers, for example dissolvers or rotor-stator mixers.

The present invention also relates to the suspensions prepared by the above-described process, which are hereinbelow termed "suspensions according to the invention".

The suspensions according to the invention act as the basis for the preparation of SCs, WGs and WPs, are storage-stable and need not be processed directly.

The subsequent list gives examples of suitable active ingredients a), but is not restricted thereto:

For example, the following active ingredients may be mentioned from the class of the fungicides:

cyprodinil, dinocap, dodemorph, dodemorph acetate, fenpropidin, fenpropimorph, flusilazole, imazalil, myclobutanil, nitrothal-isopropyl, penconazole, propamocarb hydrochloride, pyraclostrobin, spiroxamin, trifloxystrobin and propiconazole.

For example, the following active ingredients may be mentioned from the class of the herbicides:

benfluralin, bromoxynil, clodinafop-propargyl, cyhalofop-butyl, dinoterb, DNOC, ethofumesate, flamprop-M-isopropyl, flufenacet, fluoroglycofen-ethyl, flurochloridone, fluroxypyr-meptyl, haloxyfop-etotyl, haloxyfop-methyl, ioxynil octanoate, napropamide, oxyfuorifen, pendimethalin, propanil, pyridate, quizalofop-P-ethyl, quizalofop-P-tefuryl, trifluralin;

For example, the following active ingredients may be mentioned from the class of the insecticides:

alpha-cypermethrin, anilofos, azinphos-ethyl, azinphos-methyl, benzoximate, beta-cypermethrin, chlorpyrifos, cypermethrin, deltamethrin, dimethylvinphos, DNOC, endosulfan, esfenvalerate, fenoxycarb, fenvalerate, methoxychlor, metolcarb, monocrotophos, phosmet, pyridaphenthion, resmethrin, silafluofen, tetramethrin, thiofanox, triazamate, trichlorfon, xylylcarb.

In this context, the following active ingredients a) are preferred: pyraclostrobin, pendimethalin, propanil, chlorpyrifos, trifloxystrobin and propiconazole.

Pyraclostrobin is especially preferred as active ingredient a).

Silica-based carriers which are suitable for the preparation of the suspensions according to the invention are natural or synthetic silicas synthetic silicas being preferred. In general, these take the form of what are known as hydrophilic precipitated silicas or fumed silicas. Said silicas are commercially available for example under the trade names Sipernat®, Wessalon® or Aerosil® from Degussa.

Dispersions which are suitable for the preparation of the suspensions according to the invention are anionic surfactants.

Examples of suitable anionic surfactants are alkylarylsulfonates, phenylsulfonates, alkyl sulfates, alkylsulfonates, alkyl ether sulfates, alkylaryl ether sulfates, alkyl polyglycol ether phosphates, polyaryl phenyl ether phosphates, alkyl sulfosuccinates, olefinsulfonates, paraffinsulfonates, petroleum sulfonates, taurides, sarcosides, fatty acids, alkylnaphthalenesulfonic acids, naphthalenesulfonic acids, lignosulfonic acids, condensates of sulfonated naphthalenes with formaldehyde or with formaldehyde and phenol and, if appropriate, urea, and condensates of phenolsulfonic acid, formaldehyde and urea, lignin-sulfite waste liquor and lignosulfonates, including their alkali metal salts, alkaline earth metal salts, ammonium salts and amine salts, alkyl phosphates and polycarboxylates such as, for example, polyacrylates, maleic anhydride/olefin copolymers (for example Sokalan® CP9, BASF).

Preferred in this context is the use of lignosulfonates such as Kraft lignins or lignosulfonates from what is known as the sulfite waste liquor method, for example those commercially available under the trade names Borrespese®, Vanisperse®, Ufoxane®, Diwotex® (Borregard Lignotech) and Reaxx®, Kraftsperse®, Polyfon® (Westvaco Corp.) and of naphthalenesulfonic acid condensates with formaldehyde, for example those which are commercially available under the trade names Tamol NN, Tamol NH (BASF AG) or Morwet D 425 (Witco/Crompton Corp.) and condensates of phenolsulfonic acid, formaldehyde and urea, for example those available under the trade name Tamol DN (BASF AG).

The invention furthermore relates to the preparation of agrochemical formulations, viz. suspension concentrates (SCs), water-dispersible powders (WPs) or water-dispersible granules (WGs) based on the suspensions according to the invention.

SCs are prepared by treating the suspension according to the invention with one or more further agrochemical active ingredients and/or further formulation auxiliaries which are suitable for the preparation of a suspension concentrate. Formulation auxiliaries which are suitable for the preparation of a suspension concentrate are surfactants, thickeners, antifoam agents, bactericides and antifreeze agents, which are employed in the following amounts based on the total amount of the SC prepared:

| surfactants | 4.0 to 25% by weight |
|---|---|
| thickeners | 0.1 to 5% by weight |
| antifoam agents | 0.1 to 5% by weight |
| bactericides | 0.1 to 1% by weight |
| antifreeze agents | 1.0 to 20% by weight |

If appropriate, the SC formulations according to the invention may comprise, for the purposes of pH regulation, 1–5% by weight of buffer based on the total amount of the formulation prepared, the quantity and nature of the buffer employed depending on the chemical properties of the active ingredient(s). Examples of buffers are alkali metal salts of weak inorganic or organic acids such as, for example, phosphoric acid, boric acid, acetic acid, propionic acid, citric acid, fumaric acid, tartaric acid, oxalic acid and succinic acid.

The added quantity of further active ingredient(s) may amount to 1–60% by weight, preferably 5–50% by weight, based on the total amount of the SC prepared.

If required, the resulting mixture is milled to obtain the desired particle size. Milling may be effected in a mill, for example agitated ball mill. Further suitable mills are mentioned in Mollet, H. and Grubemann, A. "Formulierungstechnik", WILEY-VCH, 2000, p. 138 et seq. To achieve the desired fineness, it may be, if appropriate, necessary to repeat the milling passage several times.

When the desired particle size distribution of preferably 40% smaller than 2 microns and 100% smaller than 12 microns is achieved, the resulting SC may be treated with thixotropes.

Suitable surfactants are anionic surfactants and nonionic surfactants, mixtures of the two being preferred.

Suitable anionic surfactants are the compounds which have already been mentioned above in the preparation of the suspensions according to the invention.

Examples of suitable nonionic surfactants are alkyl phenol alkoxylates, alcohol alkoxylates, fatty amine alkoxylates, polyoxyethylene glycerol fatty acid ester, castor oil alkoxylates, fatty acid alkoxylates, fatty acid amide alkoxylates, fatty acid polydiethanolamides, lanolin ethoxylates, fatty acid polyglycol esters, isotridecyl alcohol, fatty acid amides, methylcellulose, fatty acid esters, silicone oils, alkyl polyglycosides, glycerol fatty acid esters, polyethylene glycol, polypropylene glycol, polyethylene glycol/polypropylene glycol block copolymers, polyethylene glycol alkyl ethers, polypropylene glycol alkyl ethers, polyethylene glycol/polypropylene glycol ether block copolymers, and mixtures of these.

Preferred nonionic surfactants are polyethylene glycol/polypropylene glycol block copolymers, polyethylene glycol alkyl ethers, polypropylene glycol alkyl ethers, polyethylene glycol/polypropylene glycol ether block copolymers and mixtures of these.

Viscosity-modifying additives which are suitable for the abovementioned formulation types are compounds which confer a pseudoplastic flow behavior to the formulation, i.e. high viscosity in static condition and low viscosity when in motion. Compounds which must be mentioned in this context are, for example, polysaccharides or organic sheet minerals, such as Xanthan Gum® (Kelzan® by Kelco), Rhodopol® 23 (Rhone Poulenc) or Veegum® (by R. T. Vanderbilt) or Attaclay® (by Engelhardt), Xanthan-Gum® being used in preference.

Suitable antifoam agents for the formulations according to the invention are, for example, silicone emulsions (such as, for example, Silikon® SRE, by Wacker or Rhodorsil® by Rhodia), long-chain alcohols, fatty acids, organofluorine compounds, and mixtures of these.

Bactericides may be added to the aqueous fungicide formulation for the purposes of stabilization. Examples of suitable bactericides are Proxel® from ICI or Acticide® RS by Thor Chemie and Kathon® MK by Rohm & Haas.

Examples of suitable antifreeze agents are ethylene glycol, propylene glycol or glycerol.

To prepare WP formulations based on the suspension according to the invention,
 a) a suspension according to the invention can be mixed with one or more further agrochemical active ingredients and/or further formulation auxiliaries suitable for the preparation of a water-dispersible powder, and
 b) the suspension obtained in step a) can be dried and further processed to give a water-dispersible powder.

Formulation auxiliaries suitable for the preparation of a water-dispersible powder are understood as meaning surfactants and antifoam agents which are employed in the following proportions, based on the total amount of the WP prepared:

| surfactants | 0 to 50% by weight |
| antifoam agents | 0 to 5% by weight |

If appropriate, the WP formulations according to the invention may comprise, for the purposes of pH regulation, 1–5% by weight of buffer based on the total amount of the formulation prepared, the quantity and nature of the buffer employed depending on the chemical properties of the active ingredient(s). Examples of buffers are alkali metal salts of weak inorganic or organic acids such as, for example, phosphoric acid, boric acid, acetic acid, propionic acid, citric acid, fumaric acid, tartaric acid, oxalic acid and succinic acid.

The added quantity of further active ingredient(s) may amount to 1–60% by weight, preferably 5–50% by weight, based on the total amount of the WP prepared.

Suitable surfactants and antifoam agents have likewise already been mentioned above.

If required, the mixture obtained in a) is milled to obtain the particle size desired, i.e. a particle size distribution of, preferably, 40% smaller than 2 microns and 100% smaller than 12 microns, following the above-described procedures.

The drying process which is mentioned in step b) can be effected by procedures known to the skilled worker, such as, for example, spray drying. Reference may be made to K. Masters, spray drying (G. Goodwin Ltd. Ed. London 1979). Spraying is preferably carried out using dual-substance nozzles and centrifugal atomizers.

To prepare WG formulations based on the suspensions according to the invention,
 a) a suspension according to the invention can be mixed with one or more further agrochemical active ingredients and/or further formulation auxiliaries suitable for the preparation of water-dispersible granules, and
 b) the suspension obtained in step a) can be further processed by means of a drying process to give water-dispersible granules.

Suitable formulation auxiliaries mentioned in step a) are surfactants and antifoam agents which can be employed in the following proportions, based on the total amount of the WG prepared:

| surfactants | 0 to 50% by weight |
| antifoam agents | 0 to 5% by weight |

If appropriate, the WG formulations according to the invention may comprise, for the purposes of pH regulation, 1–5% by weight of buffer based on the total amount of the formulation prepared, the quantity and nature of the buffer employed depending on the chemical properties of the active ingredient(s). Examples of buffers are alkali metal salts of weak inorganic or organic acids such as, for example, phosphoric acid, boric acid, acetic acid, propionic acid, citric acid, fumaric acid, tartaric acid, oxalic acid and succinic acid.

Suitable surfactants and antifoam agents have likewise already been mentioned above.

The added quantity of further active ingredient(s) may amount to 1–60% by weight, preferably 5–50% by weight, based on the total amount of the WG prepared.

If required, the mixture obtained in a) is milled to obtain the particle size desired, i.e. a particle size distribution of, preferably, 40% smaller than 2 microns and 100% smaller than 12 microns, following the above-described procedures.

Drying processes which are suitable for the preparation of WGs can be effected for example analogously to the processes described in Rosch, R. Probst, Verfahrenstechnik 9 (1975), No. 2, by means of spray drying and fluidized-bed granulation. In the case of spray drying, single-substance nozzles are preferably used for the preparation of WG formulations.

However, water-dispersible granules may also be prepared from a WP prepared as described above, the WP being wetted with water and subsequently granulated by means of extrusion and disc granulation methods, for example analogously to the processes described in M. Dittgen et al., Pharmazie 35, 4 (1980) p. 237 et seq.

To widen the spectrum of action, the formulations mentioned above can, as already mentioned, be combined with further agrochemical active ingredients, which, in the latter case, can be incorporated with suitable additives. The term additive is understood as meaning a selection of the abovementioned surfactants and further additives. In the case of the SC formulation, additional active ingredients may be suspended in the aqueous phase, either dissolved or in finely milled form. In the case of a WP or WG formulation, one or more active ingredients which have been added to the suspension according to the invention during the abovementioned preparation processes are distributed homogeneously in the WP or WG formulation.

In this context, the additional active ingredient(s) can be selected from the group of the fungicides, insecticides, herbicides and/or growth regulators.

Examples of fungicidal active ingredients are:

sulfur, dithiocarbamates and their derivatives, such as iron (III) dimethyldithiocarbamate, zinc dimethyldithiocarbamate, zinc ethylenebisdithiocarbamate, manganese ethylenebisdithiocarbamate, manganese zinc ethylenediaminebisdithiocarbamate, tetramethylthiuram disulfide, ammonia complex of zinc (N,N-ethylenebisdithiocarbamate), ammonia complex of zinc (N,N'-propylenebisdithiocarbamate), zinc (N,N'-propylenebisdithiocarbamate), N,N'-polypropylenebis (thiocarbamoyl)disulfide;

nitro derivatives, such as dinitro(1-methylheptyl)phenyl crotonate, 2-sec-butyl-4,6-dinitrophenyl 3,3-dimethylacrylate, 2-sec-butyl-4,6-dinitrophenylisopropyl carbonate, diisopropyl 5-nitro-isophthalate;

heterocyclic substances, such as 2-heptadecyl-2-imidazoline acetate, 2-chloro-N-(4'-chlorobiphenyl-2-yl) nicotinamide, 2,4-dichloro-6-(o-chloroanilino)-s-triazine, O, O-diethyl phthalimidophosphonothioate, 5-amino-1-[bis(dimethylamino)phosphinyl]-3-phenyl-1,2,4-triazole, 2,3-dicyano-1,4-dithioanthraquinone, 2-thio-1,3-dithiolo[4,5-b]quinoxaline, methyl 1-(butylcarbamoyl)-2-benzimidazolecarbamate, 2-methoxycarbonylaminobenzimidazole, 2-(2-furyl)benzimidazole, 2-(4-thiazolyl)benzimidazole, N-(1,1,2,2-tetrachloroethylthio)tetrahydrophthalimide, N-trichloromethylthiotetrahydrophthalimide, N-trichloromethylthiophthalimide; N-dichlorofluoromethylthio-N',N'-dimethyl-N-phenylsulfodiamide, 5-ethoxy-3-trichloromethyl-1,2,3-thiadiazole, 2-thiocyanatomethylthiobenzothiazole, 1,4-dichloro-2,5-dimethoxybenzene, 4-(2-chlorophenylhydrazono)-3-methyl-5-isoxazolone, pyridine-2-thiol 1-oxide, 8-hydroxyquinoline or its copper salt, 2,3-dihydro-5-carboxanilido-6-methyl-1,4-oxathiine, 2,3-dihydro-5-carboxanilido-6-methyl-1,4-oxathiine 4,4-dioxide, 2-methyl-5,6-dihydro-4H-pyran-3-carboxanilide, 2-methylfuran-3-carboxanilide, 2,5-dimethylfuran-3-carboxanilide, 2,4,5-trimethylfuran-3-carboxanilide, N-cyclohexyl-2,5-dimethylfuran-3-carboxamide, N-cyclohexyl-N-methoxy-2,5-dimethylfuran-3-carboxamide, 2-methylbenzanilide, 2-iodobenzanilide, N-formyl-N-morpholine-2,2,2-trichloroethyl acetal, piperazine-1,4-diylbis-1-(2,2,2-trichloroethyl)formamide, 1-(3,4-dichloroanilino)-1-formylamino-2,2,2-trichloroethane, 2,6-dimethyl-N-tridecylmorpholine or its salts, 2,6-dimethyl-N-cyclododecylmorpholine, 1-[2-(2,4-dichlorophenyl)-4-ethyl-1,3-dioxolan-2-ylmethyl]-1H-1,2,4-triazole, 1-[2-(2,4-dichlorophenyl)-4-n-propyl-1,3-dioxolan-2-ylethyl]-1H-1,2,4-triazole, N-(n-propyl)-N-(2,4,6-trichlorophenoxyethyl)-N'-imidazolylurea, 1-(4-chlorophenoxy)-3,3-dimethyl-1-(1H-1,2,4-triazol-1-yl)-2-butanone, 1-(4-chlorophenoxy)-3,3-dimethyl-1-(1H-1,2,4-triazol-1-yl)-2-butanol, (2RS,3RS)-1-[3-(2-chlorophenyl)-2-(4-fluorophenyl)oxiran-2-yl-methyl]-1H-1,2,4-triazole, α-(2-chlorophenyl)-α-(4-chlorophenyl)-5-pyrimidinemethanol, 5-butyl-2-dimethylamino-4-hydroxy-6-methylpyrimidine, bis(p-chlorophenyl)-3-pyridinemethanol, 1,2-bis(3-ethoxycarbonyl-2-thioureido)benzene, 1,2-bis(3-methoxycarbonyl-2-thioureido)benzene;

anilinopyrimidines such as N-(4,6-dimethylpyrimidin-2-yl) aniline, N-[4-methyl-6-(1-propynyl)pyrimidin-2-yl] aniline, N-[4-meth-yl-6-cyclopropylpyrimidin-2-yl] aniline;

phenylpyrroles such as 4-(2,2-difluoro-1,3-benzodioxol-4-yl)pyrrole-3-carbonitrile;

cinnamides such as 3-(4-chlorophenyl)-3-(3,4-dimethoxyphenyl) acryloylmorpholine, 3-(4-fluorophenyl)-3-(3,4-dimethoxyphenyl)acryloylmorpholine;

and a variety of fungicides such as dodecylguanidine acetate, 1-(3-bromo-6-methoxy-2-methylphenyl)-1-(2,3,4-trimethoxy-6-methyl phenyl)methanone, 3-[3-(3,5-dimethyl-2-oxycyclohexyl)-2-hydroxyethyl]glutarimide, hexachlorobenzene, methyl N-(2,6-dimethylphenyl)-N-(2-furoyl)-DL-alaninate, DL-N-(2,6-dimethylphenyl)-N-(2'-methoxyacetyl)alanine methyl ester, N-(2,6-dimethylphenyl)-N-chloroacetyl-D,L-2-aminobutyrolactone, DL-N-(2,6-dimethylphenyl)-N-(phenylacetyl)alanine methyl ester, 5-methyl-5-vinyl-3-(3,5-dichlorophenyl)-2,4-dioxo-1,3-oxazolidine, 3-(3,5-dichlorophenyl)-5-methyl-5-methoxymethyl-1,3-oxazolidine-2,4-dione, 3-(3,5-dichlorophenyl)-1-isopropyl-carbamoylhydantoin, N-(3,5-dichlorophenyl)-1,2-dimethylcyclo-propane-1,2-dicarboximide,2,4-difluoro-α-(1H-1,2,4-triazolyl-1-methyl)-benzhydrylalcohol,N-(3-chloro-2,6-dinitro-4-trifluoromethylphenyl)-5-trifluoromethyl-3-chloro-2-aminopyridine,1-((bis(4-fluorophenyl)methylsilyl)methyl)-1H-1,2,4-triazole,5-chloro-2-cyano-4-p-tolylimidazole-1-sulfodimethylamide,3,5-dichloro-N-(3-chloro-1-ethyl-1-methyl-2-oxopropyl)-4-methyl-benzamide;

strobilurins such as methyl E-methoxyimino-[α-(o-tolyloxy)-o-tolyl]acetate, methyl E-2-{2-[6-(2-cyanophenoxy)-pyrimidin-4-yloxy]phenyl}-3-methoxyacrylate, N-methyl-E-methoxyimino-(α-(2-phenoxyphenyl)]-acetamide, N-methyl-E-methoxyimino-[α-(2,5-dimethylphenoxy)-o-tolyl] acetamide, methyl E-2-{2-[2-trifluoromethylpyridyl-6-]oxymethyl] phenyl}3-methoxyacrylate, (E)-o-(2,5-dimethylphenoxymethyl)-2-methoxyimino-N-methylphenylacetamide; and nicotinanilide derivatives of the formula I:

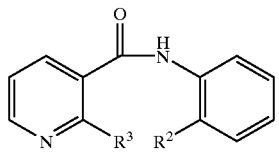

(I)

in which

R² is phenyl which is substituted by halogen atoms such as fluorine, chlorine and/or bromine, a mono- to trisubstitution being preferred; and $R^3$ is halogen, halogen being understood as meaning fluorine, chlorine or bromine, especially preferably chlorine.

An especially preferred nicotinanilide derivative of the formula I is nicobifen.

The preparation of the compounds of the formula I is disclosed in, for example, EP-A-545 099 or EP-A-589 301 or can be effected by analogous methods.

The following insecticides can be used:

neonicotinoids/chloronicotinyl compounds (such as imidacloprid, acetamiprid, nitenpyram, thiacloprid, thiamethoxam, MIT-446 (terafuranitdine) pyrroles (such as chlorphenapyr, fludioxonil) organophosphates (such as acephate, dimethoate, disulfoton, fosthiazate, methamidophos, methidathion, methyl-parathion, oxydemeton-methyl, phorate, phosalone, profenofos, malathion, phosphamidon, fenitrothion, diazinon, EPN) carbamates (such as alanycarb, aldicarb, benfuracarb, carbofuran, carbosulfan, furathiocarb, methomyl, oxamyl, pirimicarb, thiodicarb, fenobucarb) pyrethroids (such as bifenthrin, cyfluthrin, ethofenprox, fenpropathrin, flucythrinate, fluvalinate, lambda-cyhalothrin, permethrin, pyrethrin I, pyrethrin II, tau-fluvalinate, tralomethrin, zeta-cypermethrin) urea derivatives (such as diflubenzuron, flucycloxuron, flufenoxuron, hexaflumuron, lufenuron, novaluron, triflumuron) juvenoids (such as buprofezin, diofenolan, pyriproxifen, methoxyfenozide, tebufenozide) various (such as abamectin, spinosad, amitraz, cartap, chlorfenapyr, diafenthiuron, fipronil, imidacloprid, pyridaben, tebufenpyrad, nidinotefuran (MTI-446), (The 1998 Brighton Conference "Pest and Diseases", Conference Proceedings, Vol 1, page 81, fenazaquin, fenpyroxymate, thiocyclam), nidinotefuran (MTI-446) and clothionidin ((E)-1-(2-chlorothiazol-5-ylmethyl)-3-methyl-2-nitroguanidine (TI-435; Takeda, Japan)).

Examples of herbicidal active ingredients are 1,3,4-thiadiazoles (such as buthidazole, cyprazole), amides (such as allidochlor (CDAA), benzoylprop-ethyl, bromobutide, chlorthiamid, dimepiperate, dimethenamid, s-dimethenamid, diphenamid, etobenzanid (benzchlomet), fluthiamide, fosamin, isoxaben, monalide, naptalame, pronamid (propyzamid)) aminophosphoric acids (such as bilanafos, (bialaphos), buminafos, glufosinate-ammonium, glyphosate, sulfosate), aminotriazoles (such as amitrol), anilides (such as mefenacet), aryloxyalkanoic acids (such as 2,4-D, 2,4-DB, clomeprop, dichlorprop, dichlorprop-p, dichlorprop-p (2,4-DP-P), fenoprop (2,4,5-TP), fluoroxypyr, MCPA, MCPB, mecoprop, mecoprop-P, napropanilide, triclopyr, N-(1-cyano-1,2-dimethylpropyl)-2-(2,4-dichlorophenoxy)propion-amide), benzoic acids (such as chloramben, dicamba), benzothiadiazinones (such as bentazone), bleachers (such as clomazone (dimethazone), diflufenican, fluorochloridone, flupoxam, fluridone, pyrazolate, sulcotrione (chlormesulone), isoxaflutole, isoxachlortole, mesotrione), carbamates (such as asulam, barban, butylate, carbetamid, chlorbufam, chlorpropham, cycloate, desmedipham, di-allate, EPTC, esprocarb, molinate, orbencarb, pebulate, phenisopham, phenmedipham, propham, prosulfocarb, pyributicarb, sulfallate (CDEC), terbucarb, thiobencarb (benthiocarb), tiocarbazil, tri-allate, vernolate) quinolinecarboxylic acids (such as quinclorac, quinmerac), chloroacetanilides (such as acetochlor, alachlor, butachlor, butenachlor, diethatyl-ethyl, dimethachlor, metazachlor, metolachlor, pretilachlor, propachlor, prynachlor, terbuchlor, thenylchlor, xylachlor, s-metolachlor), cyclohexenones (such as alloxydim, tepraloxydim, clethodim, cloproxydim, cycloxydim, sethoxydim, tralkoxydim, 2-{1-[2-(4-chlorophenoxy)propyloxyimino]butyl}-3-hydroxy-5-(2H-tetrahydrothiopyran-3-yl)-2-cyclohexen-1-one, butroxydim, clefoxydim), dichloropropionic acids (such as dalapon), dihydrofuran-3-ones (such as flurtamone), dinitroanilines (such as benefin, butralin, dinitramin, ethalfluralin, fluchloralin, isopropalin, nitralin, oryzalin, prodiamine, profluralin) dinitrophenols (such as bromofenoxim, dinoseb, dinoseb-acetate), diphenyl ethers (such as acifluorfen-sodium, aclonifen, bifenox, chlornitrofen (CNP), difenoxuron, ethoxyfen, fluorodifen, fomesafen, furyloxyfen, lactofen, nitrofen, nitrofluorfen, oxyfluorfen), dipyridylenes (such as cyperquat, difenzoquat-methylsulfate, diquat, paraquat-dichloride) ureas (such as benzthiazuron, buturon, chlorbromuron, chloroxuron, chlortoluron, cumyluron, dibenzyluron, cycluron, dimefuron, diuron, dymron, ethidimuron, fenuron, fluormeturon, isoproturon, isouron, karbutilate, linuron, methabenzthiazuron, metobenzuron, metoxuron, monolinuron, monuron, neburon, siduron, tebuthiuron, trimeturon) imidazoles (such as isocarbamid) imidazolinones (such as imazamethapyr, imazapyr, imazaquin, imazethabenz-methyl (imazame), imazethapyr, imazapic), oxadiazoles (such as methazole, oxadiargyl, oxadiazon) oxiranes (such as tridiphane) phenoxyphenoxypropionic esters (such as cloquintocet, cyhalofop-butyl, diclofop-methyl, fenoxaprop-ethyl, fenoxaprop-p-ethyl, fenthiapropethyl, fluazifop-butyl, fluazifop-p-butyl, isoxapyrifop, propaquizafop), phenylacetic acids (such as chlorfenac (fenac)), phenylpropionic acids (such as chlorfenprop-methyl), protoporphyrinogen IX oxidase inhibitors (such as benzofenap, cinidon-ethyl, flumiclorac-pentyl, flumioxazin, flumipropyn, flupropacil, fluthiacet-methyl, pyrazoxyfen, sulfentrazone, thidiazimin, carfentrazone), pyrazoles (such as nipyraclofen, ET 751), pyridazines (such as chloridazon, maleic hydrazide, norflurazon), pyridinecarboxylic acids (such as clopyralid, dithiopyr, picloram, thiazopyr, diflufenzopyr), pyrimidyl ethers (such as pyrithiobac-acid, pyrithiobac-sodium, KIH-2023, KIH-6127, pyribenzoxym), sulfonamides (such as flumetsulam, metosulam), sulfonylureas (such as amidosulfuron, azimsulfuron, bensulfuron-methyl, chlorimuron-ethyl, chlorsulfuron, cinosulfuron, cyclosulfamuron, ethametsulfuron-methyl, ethoxysulfuron, flazasulfuron, halosulfuron-methyl, imazosulfuron, metsulfuron-methyl, nicosulfuron, primisulfuron, prosulfuron, pyrazosulfuron-ethyl, rimsulfuron, sulfometuron-methyl, thifensulfuron-methyl, triasulfuron, tribenuron-methyl, triflusulfuron-methyl, N-[[[4-methoxy-6-(trifluoromethyl)-1,3,5-triazin-2-yl]amino]-carbonyl]-2-(trifluoromethyl)benzenesulfonamide, sulfosulfuron, idosulfuron), triazines (such as ametryn, atrazine, aziprotryn, cyanazine, cyprazine, desmetryn, dimethamethryn, dipropetryn, eglinazine-ethyl, hexazinone, procyazine, prometon, prometryn, propazine, secbumeton, simazine, simetryn, terbumeton, terbutryn, terbutylazin, trietazine), triazinones (such as ethiozin, metamitron, metribuzin), triazolecarboxamides (such as triazofenamid), uracils (such as bromacil, lenacil, terbacil), and a variety of herbicides (such as benazolin, benfuresate, bensulide, benzofluor, butamifos, cafenstrole, chlorthal-dimethyl (DCPA), cinmethylin, dichlobenil, endothall, fluorbentranil, mefluidide, perfluidone, piperophos, flucabazone, oxaciclomefone (MY 100)).

The following list of compounds which have a growth-regulatory action identifies possible active ingredients, but is not intended to be limited thereto:

1-naphthylacetamide, 1-naphthylacetic acid, 2-naphthyloxyacetic acid, 3-CPA, 4-CPA, ancymidol, anthraquinone, BAP, butifos; tribufos, butralin, chlorflurenol, chlormequat, clofencet, cyclanilide, daminozide, dicamba, dikegulac-sodium, dimethipin, chlorfenethol, etacelasil, ethephon, ethychlozate, fenoprop, 2,4,5-TP, fluoridamid, flurprimidol, flutriafol, gibberellic acid, gibberellin, guazatine, indolylbutyric acid, indolylacetic acid, karetazan, kinetin, lactidichlor-ethyl, maleic hydrazide, mefluidide, mepiquat-chloride, naptalam, paclobutrazole, prohexadione-calcium, quinmerac, sintofen, tetcyclacis, thidiazuron, triiodobenzoic acid, triapenthenol, triazethan, tribufos, trinexapac-ethyl, uniconazole.

The additional active ingredient(s) is/are especially preferably selected from the following group of active ingredients: carbendazim, thiophanate-methyl, epoxiconazole, metconazole, prochloraz, propiconazole, quinoxyfen, folpet, dithianon, captan, dimethomorph, IKF 916, iprovalicarb, proazolthion, metiram, mancozeb, kresoxim-methyl, azoxystrobin, picoxystrobin, N-methylphenyl-(E)-o-(2,5-dimethylphenoxymethyl)-2-methoxyimino-acetamide and nicotinanilide derivatives of the formula I such as nicobifen, with N-methylphenyl-(E)-o-(2,5-dimethylphenoxymethyl)-2-methoxyimino-acetamide, nicotinanilide derivatives of the formula I such as nicobifen, folpet, metiram, dithianon and dimethomorph being employed very especially preferably.

The present invention furthermore relates to a method of regulating the growth of plants, for the control of undesired vegetation, undesired attack by insects or mites, and/or a method for controlling phytopathogenic fungi.

Phytopathogenic fungi which can be controlled by the formulations according to the invention are understood as meaning, for example, the following species:

Alternaria species, Podosphaera species, Sclerotinia species, *Physalospora canker* on vegetables and fruit, *Botrytis cinerea* (gray mold) on strawberries, vegetables, ornamentals and grapevines, *Corynespora melonis* on cucumbers, strawberries; Colletotrichum species on cucumbers; *Diplocarpon rosae* on roses; *Elsinoe fawcetti* and *Diaporthe citri* on citrus fruit; Sphaerotheca species on cucumbers, cucurbits, strawberries and roses; Cercospora species on peanuts, sugarbeet, egg plants and date palms; *Erysiphe cichoracearum* and *Sphaerotheca fuliginea* on cucurbits, *Leveiillina taurica* on pimento; Mycosphaerella species on apples and Japanese apricot; *Phyllactinia kakicola, Gloesporium kaki* on Japanese apricot; *Gymnosporangium yamadae, Leptotthrydium pomi, Podosphaera leucotricha* and *Gloedes pomigena* on apples; *Cladosporium carpophilum* on pears and Japanese apricot; Phomopsis species on pears; Phytophthora species on citrus fruits, potatoes, onions; *Phytophthora infestans* on potatoes and tomatoes, *Erysiphe graminis* (powdery mildew) on cereals, Fusarium and Verticillium species on a variety of plants, *Glomerella cingulata* on tea; Helminthosporium species on cereals, Mycosphaerella species on bananas and peanuts, *Plasmopara viticola* on grapevines and grapefruits, Peronospora species on onions, spinach and chrysanthemums; *Phaeoisariopsis vitis* and *Spaceloma ampelina* on grapefruits; *Pseudocercosporella herpotrichoides* on wheat and barley, Pseudoperonospora species on hops and cucumbers, Puccinia species and Typhula species on cereals, *Pyricularia oryzae* on rice, Rhizoctonia species on cotton, rice and turf, *Septoria nodorum* on wheat, *Uncinula necator* on grapevines, Ustilago species on cereals and sugarcane, and Venturia species (scab) on apples and pears.

Insects which can be controlled by the formulations according to the invention include, for example, insects from the order of the Lepidoptera (butterflies and moths), for example *Agrotis ypsilon, Agrotis segetum, Alabama argillacea, Anticarsia gemmatalis, Argyresthia conjugeila, Autographa gamma, Bupalus piniarius, Cacoecia murinana, Capua reticulana, Cheimatobia brumata, Choristoneura fumiferana, Choristoneura occidentalis, Cirphis unipuncta, Cydia pomonella, Dendrolimus pini, Diaphania nitidalis, Diatraea grandiosella, Earias insulana, Elasmopalpus lignosellus, Eupoecilia ambiguella, Evetria bouliana, Feltia subterranea, Galleria mellonella, Grapholitha funebrana, Grapholitha molesta, Heliothis armigera, Heliothis virescens, Heliothis zea, Hellula undalis, Hibernia defoliaria, Hyphantria cunea, Hyponomeuta malinellus, Keiferia lycopersicella, Lambdina fiscellaria, Laphygma exigua, Leucoptera coffeella, Leucoptera scitella, Lithotis blancardella, Lobesia botrana, Loxostege sticticalis, Lymantria dispar, Lymantria monacha, Lyonetia clerkella, Malacosoma neustria, Mamestra brassicae, Orgyia pseudotsugata, Ostrinia nubilalis, Panolis flammea, Pectinophora gossypiella, Peridroma saucia, Phalera bucephala, Phthorimaea operculella, Phyllocnistis citrella, Pieris brassicae, Plathypena scabra, Plutella xylostella, Pseudoplusia includens, Rhyacionia frustrana, Scrobipalpula absoluta, Sitotroga cerealella, Sparganothis pilleriana, Spodoptera frugiperda, Spodoptera littoralis, Spodoptera litura, Thaumatopoea pityocampa, Tortrix viridana, Trichoplusia ni* and *Zeiraphera canadensis,* from the order of the Coleoptera (beetles), for example *Agrilus sinuatus, Agriotes lineatus, Agriotes obscurus, Amphimallus solstitialis, Anisandrus dispar, Anthonomus grandis, Anthonomus pomorum, Atomaria linearis, Blastophagus piniperda, Blitophaga undata, Bruchus rufimanus, Bruchus pisorum, Bruchus lentis, Byctiscus betulae, Cassida nebulosa, Cerotoma trifurcata, Ceuthorrhynchus assimilis, Ceuthorrhynchus napi, Chaetocnema tibialis, Conoderus vespertinus, Crioceris asparagi, Diabrotica longicornis, Diabrotica 12-punctata, Diabrotica virgifera, Epilachna varivestis, Epitrix hirtipennis, Eutinobothrus brasiliensis, Hylobius abietis, Hypera brunneipennis, Hypera postica, Ips typographus, Lema bilineata, Lema melanopus, Leptinotarsa decemlineata, Limonius californicus, Lissorhoptrus oryzophilus, Melanotus communis, Meligethes aeneus, Melolontha hippocastani, Melolontha melolontha, Oulema oryzae, Otiorrhynchus sulcatus, Otiorrhynchus ovatus, Phaedon cochleariae, Phyllotreta chrysocephala,* Phyllophaga sp., *Phyllopertha horticola, Phyllotreta nemorum, Phyllotreta striolata, Popillia japonica, Sitona lineatus* and *Sitophilus granaria,* from the order of the Diptera (dipterans), for example *Aedes aegypti, Aedes vexans, Anastrepha ludens, Anopheles*

*maculipennis, Ceratitis capitata, Chrysomya bezziana, Chrysomya hominivorax, Chrysomya macellaria, Contarinia sorghicola, Cordylobia anthropophaga, Culex pipiens, Dacus cucurbitae, Dacus oleae, Dasineura brassicae, Fannia canicularis, Gasterophilus intestinalis, Glossina morsitans, Haematobia irritans, Haplodiplosis equestris, Hylemyia platura, Hypoderma lineata, Liriomyza sativae, Liriomyza trifolii, Lucilia caprina, Lucilia cuprina, Lucilia sericata, Lycoria pectoralis, Mayetiola destructor, Musca domestica, Muscina stabulans, Oestrus ovis, Oscinella frit, Pegomya hysocyami, Phorbia antiqua, Phorbia brassicae, Phorbia coarctata, Rhagoletis cerasi, Rhagoletis pomonella, Tabanus bovinus, Tipula oleracea* and *Tipula paludosa,* from the order of the Thysanoptera, for example *Frankliniella fusca, Frankliniella occidentalis, Frankliniella tritici, Scirtothrips citri, Thrips oryzae, Thrips palmi* and *Thrips tabaci,* from the order of the Hymenoptera, for example *Athalia rosae, Atta cephalotes, Atta sexdens, Atta texana, Hoplocampa minuta, Hoplocampa testudinea, Monomorium pharaonis, Solenopsis geminata* and *Solenopsis invicta,* from the order of the Heteroptera, for example *Acrosternum hilare, Blissus leucopterus, Cyrtopeltis notatus, Dysdercus cingulatus, Dysdercus intermedius, Eurygaster integriceps, Euschistus impictiventris, Leptoglossus phyllopus, Lygus lineolaris, Lygus pratensis, Nezara viridula, Piesma quadrata, Solubea insularis* and *Thyanta perditor,* from the order of the Homoptera, for example *Acyrthosiphon onobrychis, Adelges laricis, Aphidula nasturtii, Aphis fabae, Aphis pomi, Aphis sambuci, Brachycaudus cardui, Brevicoryne brassicae, Cerosipha gossypii, Dreyfusia nordmannianae, Dreyfusia piceae, Dysaphis radicola, Dysaulacorthum pseudosolani, Empoasca fabae, Macrosiphum avenae, Macrosiphum euphorbiae, Macrosiphon rosae, Megoura viciae, Metopolophium dirhodum, Myzodes persicae, Myzus cerasi, Nilaparvata lugens, Pemphigus bursarius, Perkinsiella saccharicida, Phorodon humuli, Psylla mali, Psylla piri, Rhopalomyzus ascalonicus, Rhopalosiphum maidis, Sappaphis mala, Sappaphis mali, Schizaphis graminum, Schizoneura lanuginosa, Trialeurodes vaporariorum* and *Viteus vitifolii,* from the order of the Isoptera, for example *Calotermes flavicollis, Leucotermes flavipes, Reticulitermes lucifugus* and *Termes natalensis,* from the order of the Orthoptera, for example *Acheta domestica, Blatta orientalis, Blattella germanica, Forficula auricularia, Gryllotalpa gryllotalpa, Locusta migratoria, Melanoplus bivittatus, Melanoplus femurrubrum, Melanoplus mexicanus, Melanoplus sanguinipes, Melanoplus spretus, Nomadacris septemfasciata, Periplaneta americana, Schistocerca americana, Schistocerca peregrina, Stauronotus maroccanus* and *Tachycines asynamorus,* from the order of the Acari, for example *Amblyomma americanum, Amblyomma variegatum, Argas persicus, Boophilus annulatus, Boophilus decoloratus, Boophilus microplus, Brevipalpus phoenicis, Bryobia praetiosa, Dermacentor silvarum, Eotetranychus carpini, Eriophyes sheldoni, Hyalomma truncatum, Ixodes ricinus, Ixodes rubicundus, Ornithodorus moubata, Otobius megnini, Paratetranychus pilosus, Dermanyssus gallinae, Phyllocoptruta oleivora, Polyphagotarsonemus latus, Psoroptes ovis, Rhipicephalus appendiculatus, Rhipicephalus evertsi, Sarcoptes scabiei, Tetranychus cinnabarinus, Tetranychus kanzawai, Tetranychus pacificus, Tetranychus telarius* and *Tetranychus urticae,* from the order of the nematodes such as root-knot nematodes, for example *Meloidogyne hapla, Meloidogyne incognita, Meloidogyne javanica,* cyst-forming nematodes, for example *Globodera rostochiensis, Heterodera avenae, Heterodera glycines, Heterodera schachtii, Heterodera trifolii,* stem eelworms and foliar nematodes, for example *Belonolaimus longicaudatus, Ditylenchus destructor, Ditylenchus dipsaci, Heliocotylenchus multicinctus, Longidorus elongatus, Radopholus similis, Rotylenchus robustus, Trichodorus primitivus, Tylenchorhynchus claytoni, Tylenchorhynchus dubius, Pratylenchus neglectus, Pratylenchus enetrans, Pratylenchus curvitatus* and *Pratylenchus goodeyi.*

Plant growth regulation can be effected by the growth regulators which have already been mentioned further above or else by the use of fertilizers.

The control of undesired vegetation is understood as meaning the destruction of weeds. Weeds, in the broadest sense, are understood as meaning all those plants which grow in locations where they are undesired, for example: Dicotyledonous weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver, Centaurea, Trifolium, Ranunculus, Taraxacum.

Monocotyledonous weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristyslis, Sagittaria, Eleocharis, Scirpus, Paspalum, Ischaemum, Sphenoclea, Dactyloctenium, Agrostis, Alopecurus, Apera.

Moreover, the formulations according to the invention can be employed in a further number of crop plants for eliminating undesired plants. Suitable crops are, for example, the following:

*Allium cepa, Ananas comosus, Arachis hypogaea, Asparagus officinalis, Beta vulgaris* spec. *altissima, Beta vulgaris* spec. *rapa, Brassica napus* var. *napus, Brassica napus* var. *napobrassica, Brassica rapa* var. *silvestris, Camellia sinensis, Carthamus tinctorius, Carya illinoinensis, Citrus limon, Citrus sinensis, Coffea arabica (Coffea canephora, Coffea liberica), Cucumis sativus, Cynodon dactylon, Daucus carota, Elaeis guineensis, Fragaria vesca, Glycine max, Gossypium hirsutum, (Gossypium arboreum, Gossypium herbaceum, Gossypium vitifolium), Helianthus annuus, Hevea brasiliensis, Hordeum vulgare, Humulus lupulus, Ipomoea batatas, Juglans regia, Lens culinaris, Linum usitatissimum, Lycopersicon lycopersicum,* Malus spec., *Manihot esculenta, Medicago sativa,* Musa spec., *Nicotiana tabacum (N.rustica), Olea europaea, Oryza sativa, Phaseolus lunatus, Phaseolus vulgaris, Picea abies,* Pinus spec., *Pisum sativum, Prunus avium, Prunus persica, Pyrus communis, Ribes sylvestre, Ricinus communis, Saccharum officinarum, Secale cereale, Solanum tuberosum, Sorghum bicolor (s. vulgare), Theobroma cacao, Trifolium pratense, Triticum aestivum, Triticum durum, Vicia faba, Vitis vinifera, Zea mays.*

A preferred embodiment of the abovementioned method is a method of controlling phytopathogenic fungi.

All the abovementioned methods of regulating the growth of plants and/or of controlling undesired plant growth and/or for controlling undesired attack by insects or mites and/or for controlling phytopathogenic fungi can be effected by formulating a suspension according to the invention in the form of a suspension concentrate, a water-dispersible powder or water-dispersible granules and applying an effective amount of the formulation prepared to undesired plants and/or to plants or seed for regulating the growth and/or to the pest in question or the materials, plants, soils, or seeds to be protected from the pest in question. The formulation of the suspensions according to the invention as SC, WP or WG formulation is described hereinabove.

In this context, the application of the compositions according to the invention may be carried out by procedures known to the skilled worker.

Thus, for example, the compositions according to the invention comprising herbicidal active ingredients can be applied pre- or post-emergence. If the active ingredients in question are less well tolerated by certain crop plants, application techniques may be used in which the dilute SC or SE formulations are spread, with the aid of the spraying apparatus, in such a way that the leaves of the sensitive crops come into as little contact as possible, if any, with the herbicidal active ingredients, while the latter reach the leaves of undesired plants which grow underneath, or the bare soil surface (post-directed, lay-by).

The compositions according to the invention comprising fungicidal active ingredients may be applied curatively, by way of eradication or protectively.

The application rates of active ingredient are from 0.001 to 10 kg/ha, preferably from 0.01 to 5 kg/ha, depending on the envisaged aim, the season, the target crops and the growth stage.

The method according to the invention will be illustrated in the following text by way of examples, but is not limited thereto:

EXAMPLE 1

Preparation of the Suspensions According to the Invention

The trade names of the adjuvants used for the suspensions and formulations according to the invention described hereinbelow are compiled in Table 1.

TABLE 1

| Name | Chemical name | Supplier |
|---|---|---|
| Ufoxane ® 3A | Lignosulfonate | Borregard Lignotech |
| Wettol ® D1 | Condensate of phenol-sulfonic acid, urea and formaldehyde | BASF Aktiengesellschaft |
| Tamol ® NH | Condensate of phenol-sulfonic acid, urea and formaldehyde | BASF Aktiengesellschaft |
| Diwatex ® 200 | Lignosulfonate | Borregard Lignotech |
| Sipernat ® FK 350 | Silica | Degussa |
| Sipernat ® 22 | Silica | Degussa |
| Pluronic ® PE 10500 | EO/PO block copolymer | BASF Aktiengesellschaft |
| Kelzan ® | Xanthan Gum | Kelco |
| Silikon ® SRE | Silicone oil emulsion | Wacker Chemie |
| Proxel ® GXL | Aqueous dipropylene glycol solution comprising 20% 1,2-benzisothiazolin-3-one | ICI |

A) Preparation of a Concentrate with an Active Ingredient Content of 15% by Weight 645 g of water were mixed with 150 g of Sipernat® FK 350 and 53 g of Ufoxane® 3A and the mixture was warmed to 80° C. 152 g of molten pyraclostrobin (98%) were added with stirring (disperse disc 1800 rpm) over a period of 5 minutes with subsequent incubation for 30 minutes at the same stirring speed. After the heater had been removed, the resulting suspension was cooled to room temperature with stirring.

B) Preparation of Concentrates with an Active Ingredient Content of Approx. 20% by Weight The suspensions S-1 to S-6 according to the invention which are listed in Table 2 were prepared following the protocol described hereinbelow.

600 g of water were mixed with 150 g of silica (see Table 2) and 53 g of dispersant (see Table 2), and the mixture was warmed to 80° C. 200 g of molten pyraclostrobin (98%) were added with stirring (disperse disc 1800 rpm) over a period of 5 minutes with subsequent incubation for 30 minutes at the same stirring speed. After the heater had been removed, the resulting suspension was cooled to room temperature with stirring.

TABLE 2

| Preparation No. | Silica | Dispersant |
|---|---|---|
| S-1 | Sipernat ® FK350 | Ufoxane ® 3A |
| S-2 | Sipernat ® FK350 | Wettol ® D1 |
| S-3 | Sipernat ® FK350 | Diwotex ® 200 |
| S-4 | Sipernat ® 22 | Wettol ® D1 |
| S-5 | Sipernat ® 22 | Diwatex ® 200 |
| S-6 | Sipernat ® FK350 | Diwatex ® 200 |

EXAMPLE 2

Preparation of Suspension Concentrates

General Protocol

Approx. 200 ml of water were introduced into a container, and the amounts of Wettol D1 stated in Table 3, 30 g of Pluronic® PE 10500, 70 g of propylene glycol and fumaric acid were added and the mixture was homogenized. The second active ingredient was added to this mixture, and the batch was subsequently treated with one of the suspensions S-1 to S-6 according to the invention prepared in Example 1B). The resulting suspension is ground by means of an agitated ball mill, if necessary brought to pH 6 using 25% by weight NaOH, and thickened with the amount of xanthan gum stated in Table 3, which had been predispersed in 15 ml of water. The volume of the suspension was made up to 1000 ml with water.

Six suspension concentrates SC-1 to SC-6, whose composition is shown in Table 3, were prepared following the above protocol.

TABLE 3

Composition of the formulations SC No. 1–6

| No. | Wettol D1 [g] | Fumaric acid [g] | Xanthan Gum | Preparation from Table 2 | Active ingredient 2 |
|---|---|---|---|---|---|
| SC-1 | 19 | 12 | 3 | 1 | 400 g folpan |
| SC-2 | 19 | 12 | 3 | 2 | 400 g folpan |
| SC-3 | 19 | 12 | 3 | 3 | 400 g folpan |
| SC-4 | 19 | 12 | 3 | 4 | 400 g folpan |
| SC-5 | 19 | 12 | 3 | 5 | 400 g folpan |

TABLE 3-continued

Composition of the formulations SC No. 1–6

| No. | Wettol D1 [g] | Fumaric acid [g] | Xanthan Gum | Preparation from Table 2 | Active ingredient 2 |
|---|---|---|---|---|---|
| SC-6 | 20 | — | 1 | 6 | 200 g 2-chloro-N-(4'-chlorobiphenyl-2-yl)nicotinamide |
| SC-7 | 20 | — | 1 | 2 | 200 g 2-chloro-N-(4'-chlorobiphenyl-2-yl)nicotinamide |

EXAMPLE 3

Physico-chemical Properties of the Resulting Formulations, and Comparative Experiments The resulting formulations were subsequently examined for the stability of the dispersion (CIPAC Method, MT 180). The results are compiled in Table 4.

TABLE 4

| | Stability of the dispersion [ml precipitate] | | | |
|---|---|---|---|---|
| | immediately post-preparation | after 1 month storage | | |
| Name (from Table 3) | 20° C. | 20° C. | 40° C. | 50° C. |
| SC-1 | <0.05 | 0.4 | 4.5 | 2.8 |
| SC-3 | <0.05 | 0.2 | 0.2 | 0.15 |
| SC-2 | <0.05 | 0.15 | 0.05 | 0.3 |
| SC-4 | <0.05 | <0.05 | 0.1 | 0.25 |
| SC-5 | <0.05 | <0.05 | 0.2 | 0.25 |
| SC-6 | 0.15 | <0.05 | 0.3 | 0.5 |
| SC-7 | 0.4 | <0.05 | <0.05 | 0.2 |

EXAMPLE 4

Preparation of WGs

A) WGs Comprising Pyraclostrobin and Metiram

In a container, a mixture of 4700 g of water, 40 g of Silikon® SRE, 966 g of Ufoxane® 3A, 483 g of Tamol® NH and 3040 g of metiram is prepared with stirring, 1760 g of a suspension according to the invention prepared in analogy to the protocol in Example 1A consisting of 15.9% by weight of pyraclostrobin, 15.9% by weight of Ufoxane® 3A, 6.3% by weight of Sipernat® FK350 are added, and the mixture is subsequently milled in a bead mill. After addition of 380 g of formaldehyde solution (40%), the mixture is dried by spray drying in a pilot-scale spray tower (by Niro) using a single-substance nozzle at a tower entrance temperature of 170° C. This gives water-dispersible granules.

B) WGs comprising pyraclostrobin and 2-chloro-N-(4'-chlorobiphenyl-2-yl)nicotinamide In a container, a mixture of 5860 g of water, 500 g of ammonium sulfate, 40 g of Silikon® SRE, 1490 g of Ufoxane® 3A, 746 of Tamol® NH and 1330 g of 2-chloro-N-(4'-chlorobiphenyl-2-yl)nicotinamide was prepared with stirring, 2390 g of a suspension according to the invention prepared in analogy to the protocol given in Example 1A, composed of 14% by weight of pyraclostrobin, 14% by weight of Ufoxane® 3A and 5.5% by weight of Sipernat® FK350 were added, and the mixture was subsequently milled in a bead mill. Three quarters of the milled mixture was then dried by spray drying in a pilot-scale spray tower (by Niro) with a single-substance nozzle, the air having a tower entrance temperature of 170° C. One quarter of the milled mixture was dried by fluidized-bed granulation in a pilot-scale fluidized-bed granulator (by Aeromatic), the air having an entrance temperature of 120° C. Both processes give water-dispersible granules.

C) WGs Comprising Pyraclostrobin and Dimethomorph

In a container, a mixture of 2230 g of water, 500 g of kaolin, 20 g of Silikon® SRE, 829 g of Tamol® NH, 415 g of Ufoxane® 3A and 309 g of dimethomorph was prepared with stirring, 1197 g of a suspension concentrate according to the invention prepared in analogy to the protocol given in Example 1A, consisting of 14% by weight of pyraclostrobin, 14% by weight of Ufoxane® 3A and 5.5% by weight of Sipernat® FK350 was added, and the mixture was subsequently milled in a bead mill. Three quarters of the milled mixture was then dried by spray drying in a pilot-scale spray tower (by Niro) with a single-substance nozzle, the air having a tower entrance temperature of 170° C. One quarter of the milled mixture was dried by fluidized-bed granulation in a pilot-scale fluidized-bed granulator (by Aeromatic), the air having an entrance temperature of 120° C. Both processes give water-dispersible granules.

We claim:

1. A process for the preparation of an aqueous suspension comprising
   from 1–25% by weight of one or more water-insoluble solid agrochemical active ingredient(s) having a melting point of <80°C.,
   from 1–40% by weight of a silica-based carrier,
   from 1–40% by weight of anionic dispersant, and
   from 40–97% by weight of water,
wherein the weight percentages amount to a total of 100%, which process comprises
   a) providing a melt (i) of the active ingredient(s),
   b) providing a suspension (ii) of the 1–40% by weight of the carrier, the 40 to 97% by weight of the water, and the 1–40% by weight of the anionic dispersant, and heating the suspension to a temperature above the temperature of the melt (i), and
   c) adding, with stirring, 1–25% by weight of the melt (i) to the heated suspension (ii).

2. A process as claimed in claim 1, wherein each of the one or more solid active ingredient(s) is selected from the group consisting of flufenacet, cyprodinil, dinocap, DNOC, dodemorph, dodemorph acetate, fenpropidin, fenpropimorph, flusilazole, imazalil, myclobutanil, nitrothal-isopropyl, penconazole, propamocarb hydrochloride, pyraclostrobin, spiroxamin, benfluralin, bromoxynil, clodinafop-propargyl, cyhalofop-butyl, dinoterb, DNOC, ethofumesate, fluoroglycofen-ethyl, flurochloridone, fluroxypyr-meptyl, haloxyfop-etotyl, haloxyfop-methyl, ioxynil octanoate, napropamide, oxyfuorifen, pendimethalin, propanil, pyridate, quizalofop-P-ethyl, quizalofop-P-tefuryl, trifluralin, alpha-cypermethrin, anilofos, azinphos-ethyl, azinphos-methyl, benzoximate, beta-cypermethrin, chiorpyrifos, cypermethrin, deltamethrin, dimethylvinphos, endosulfan, esfenvalerate, fenoxycarb, fenvalerate, flamprop-M-isopropyl, methoxychlor, metolcarb, monocrotophos, phosmet, pyridaphenthion, resmethrin, silafluofen, tetramethrin, thiofanox, triazamate, trichlorf on, trifloxystrobin and xylylcarb.

3. A process as claimed in claim 1, wherein each of the one or more solid active ingredient(s) is selected from the group consisting of pendimethalin, propanil pyraclostrobin and trifloxystrobin.

4. A suspension obtainable by the process as claimed in claim 1.

5. A suspension as claimed in claim 4, wherein a precipitated silica is used as the carrier.

6. A suspension as claimed in claim 4, wherein the dispersant is selected from the group of the lignosulfonates, of the condensates of sulfonated naphthalenes with formaldehyde or with formaldehyde and phenol and, if appropriate urea, and condensates of phenolsulfonic acid, formaldehyde and urea.

7. A process for the preparation of a suspension concentrate, which comprises mixing a suspension as claimed in claim 4 with one or more further agrochemical active substance(s) and/or further formulation auxiliaries suitable for the preparation of the suspension concentrate.

8. A process for the preparation of a water-dispersible powder, which comprises
   a) mixing a suspension as claimed in claim 4 with one or more further agrochemical active substance(s) and/or further formulation auxiliaries suitable for the preparation of a water-dispersible powder, and
   b) drying the mixture obtained in step a) and processing it to give a water-dispersible powder.

9. A process for the preparation of water-dispersible granules, which comprises
   a) mixing a suspension as claimed in claim 4 with one or more further agrochemical active substance(s) and/or further formulation auxiliaries suitable for the preparation of water-dispersible granules, and
   b) processing the mixture obtained in step a) by means of a drying process to give water-dispersible granules.

10. A process as claimed in claim 7, wherein the further agrochemical active substance is one or more compounds selected from the group consisting of carbendazim, thiophanatemethyl, epoxiconazole, metconazole, prochloraz, propiconazole, quinoxyfen, folpan, captan, dimethomorph, kresoxim-methyl, azoxystrobin, picoxystrobin, IKF 916, iprovalicarb, proazoithion, metiram, mancozeb, dithianon, cyprodinil, N-methylphenyl-(E)-o-(2, 5-dimethyiphenoxymethyl)-2-methoxyiminoacetamide and nicotinanilide derivatives of the formula I

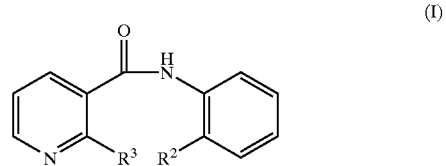

where
R² is halo-substituted phenyl and
R³ is halogen.

11. A process as claimed in claim 10, wherein the further agrochemical active substance is one or more compounds selected from the group consisting of folpan, captan, metiram, mancozeb, dithianon, dimethoraorph and nicotinanilide derivatives.

12. A method of regulating the growth of plants and/or for controlling undesired plant growth and/or for controlling undesired attack by insects or mites and/or for controlling phytopathogenic fungi, which comprises formulating a suspension as claimed in claim 4 in the form of a suspension concentrate, a water-dispersible powder or water-dispersible granules and applying an effective amount of the resulting formulation to undesired plants and/or to plants or seed for regulating the growth and/or to the pest in question and/or to the materials, plants, soils or seeds to be protected from the pest in question.

* * * * *